(12) United States Patent
Beckmann et al.

(10) Patent No.: US 7,910,573 B2
(45) Date of Patent: Mar. 22, 2011

(54) CRYSTALLINE FORMS OF 11β-(4-ACETYLPHENYL)-20,20,21,21,21-PENTAFLUORO-17-HYDROXY-19-NOR-17α-PREGNA-4,9-DIEN-3-ONE

(75) Inventors: Wolfgang Beckmann, Berlin (DE); Gabriele Winter, Schönfliess (DE); Edda Kraemer, Berlin (DE); Thomas Ginko, Berlin (DE); Evelin Amoulong, Falkensee (DE); Arwed Cleve, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 68 days.

(21) Appl. No.: 11/757,118

(22) Filed: Jun. 1, 2007

(65) Prior Publication Data
US 2008/0085875 A1    Apr. 10, 2008

Related U.S. Application Data

(60) Provisional application No. 60/810,127, filed on Jun. 2, 2006.

(30) Foreign Application Priority Data

Jun. 2, 2006 (EP) .................................... 06090095

(51) Int. Cl.
     *A01N 29/12*      (2006.01)
     *A61K 31/03*      (2006.01)
     *C07C 49/00*      (2006.01)

(52) U.S. Cl. .......................... 514/183; 568/303; 514/749
(58) Field of Classification Search .................. 514/183, 514/749; 568/303
See application file for complete search history.

(56) References Cited

U.S. PATENT DOCUMENTS

| | | | |
|---|---|---|---|
| 4,921,846 A | 5/1990 | Nedelec et al. | |
| 4,954,490 A | 9/1990 | Cook et al. | |
| 5,073,548 A | 12/1991 | Cook et al. | |
| 5,108,996 A | 4/1992 | Claussner et al. | |
| 5,407,928 A | 4/1995 | Kasch et al. | |
| 5,739,125 A | 4/1998 | Kasch et al. | |
| 6,020,328 A | 2/2000 | Cook et al. | |
| 6,316,432 B1 | 11/2001 | Schwede et al. | |
| 6,476,079 B1 | 11/2002 | Jukarainen et al. | |
| 6,503,895 B2 | 1/2003 | Schwede et al. | |
| 6,806,263 B2 | 10/2004 | Schwede et al. | |
| 6,825,182 B2 | 11/2004 | Ring et al. | |
| 6,861,415 B2 | 3/2005 | Kim et al. | |
| 7,087,591 B2 | 8/2006 | Kim et al. | |
| 7,148,213 B2 | 12/2006 | Schwede et al. | |
| 2004/0006241 A1 | 1/2004 | Grawe et al. | |
| 2004/0157811 A1 | 8/2004 | Lichtner et al. | |
| 2005/0080060 A1 | 4/2005 | Schwede et al. | |
| 2005/0277769 A1 | 12/2005 | Burton et al. | |
| 2007/0105828 A1 | 5/2007 | Joshi et al. | |

FOREIGN PATENT DOCUMENTS

| | | |
|---|---|---|
| DE | 19706061 | 8/1998 |
| DE | 10221034 | 11/2003 |
| EP | 0 411 733 | 2/1991 |
| EP | 0 676 203 | 10/1995 |
| EP | 0970103 | 1/2000 |
| EP | 0970103 B1 | 4/2002 |
| IN | 978/MUM/2005 | 8/2005 |
| JP | 11171774 | 6/1999 |
| WO | WO-98/26783 | 6/1998 |
| WO | WO-98/34947 | 8/1998 |
| WO | WO 98/34947 A | 8/1998 |
| WO | WO-99/53924 | 10/1999 |
| WO | WO-2006 010097 | 1/2006 |

OTHER PUBLICATIONS

Caira, Topics in Current Chemistry (1988) 198:163-208).*
Vippagunta et. al., Advanced Drug Delivery Reviews (2001) 48:3-26).*
Davey (Current topics in crystallization process (1982) 8:429-479).*
Ulrike Fuhrmann, et al.; "Synthesis and Biological Activity of a Novel, Highly Potent Progesterone Receptor Antagonist"; J. Med. Chem.; 2000; pp. 5010-5016; 43; American Chemical Society.
Walter Cabri, et al.; "Polymorphisms and Patent, Market and Legal Battles: Cefdinir Case Study"; Organic Process Research and Development; 2007; pp. 64-72; vol. 11, No. 1; American Chemical Society.
M. Bohl, et al.; "Molecular mechanics and X-ray crystal structure investigations on conformations of 11β substituted 4,9-dien-3-one steroids"; J. Mol. Graphics; Sep. 1989; pp. 122-153; vol. 7; Butterworth Publishers. Dario Braga, et al.; "Crystal Polymorphism: Challenges at the Crossroads of Science and Technology"; Making Crystals by Design; pp. 293-314; 2007; Wiley-VCH Verlag GmbH & Co. KGaA.
David K. Tellekson, et al.; "Strategies for Attacking and Defending Pharmaceutical Patents . . ."; Intellectual Property & Technology Law Journal; Dec. 2005; pp. 5-14; vol. 17, No. 12; Aspen Publishers, Inc.

(Continued)

*Primary Examiner* — Brandon J Fetterolf
*Assistant Examiner* — Marcos Sznaidman
(74) *Attorney, Agent, or Firm* — Millen, White, Zelano & Branigan, P.C.

(57) ABSTRACT

The present invention relates to crystalline forms of 11β-(4-acetylphenyl)-20,20,21,21,21-pentafluoro-17-hydroxy-19-nor-17α-pregna-4,9-dien-3-one. The invention relates in particular to two crystalline ansolvate/anhydrate forms of this compound, polymorphs I and II. However, the present invention also relates to crystalline solvates, for example methanol and ethanol solvates of 11β-(4-acetylphenyl)-20,20,21,21,21-pentafluoro-17-hydroxy-19-nor-17α-pregna-4,9-dien-3-one as precursors for preparing these two polymorphs I and II. Processes for preparing polymorph I by displacement crystallization or by trituration are described. Selection of the last solvent before formation of the ansolvate can be based on the differences in the purification behaviour of the individual solvates of 11β-(4-acetylphenyl)-20,20,21,21,21-pentafluoro-17-hydroxy-19-nor-17α-pregna-4,9-dien-3-one. Polymorph I according to the invention is particularly suitable for the manufacture of medicinal products.

11 Claims, 7 Drawing Sheets

OTHER PUBLICATIONS

English translation of Office Action/Minutes; EP 06 090 095.8; dated Jan. 16, 2007; with attached extended European search report.

Maibauer R., et al.; "First human data for ZK 230211 (ZK-PRA), a new progesterone receptor . . ."; Abstracts-Poster Session IV, #4074; with attached poster, dated Dec. 14, 2006.

Ulrike Fuhrmann, et al.; "Synthesis and Biological Activity of a Novel, Highly Potent Progesterone Receptor Antagonist"; Journal of Medicinal Chemistry; 2000; pp. 5010-5016; vol. 43, No. 26; American Chemical Society.

Fuhrmann U, et al.; "Synthesis and Biological Activity of a Novel, Highly Potent Progesterone Receptor Antagonist"; J. Med. Chem.; 2000; pp. 5010-5016; Bd.43 Nr.26; American Chemical Society, XP001064233.

Bohl, M. et al., "Molecular mechanics and X-reay crystal structure investigations on conformations of 11β substituted 4,9-dien-3-one steroids," J. Mol. Graphics, Sep. 1989, vol. 7.

Braga, Dario et al., "Crystal Polymorphism: Challenges at the Crossroads of Science and Technology," Making Crystals by Design, 2007, pp. 293-314.

Cabri, Walter et al., "Polymorphisms and Patent, Market, and Legal Battles: Cefdinir Case Study," Organic Process Research & Development, 2007, vol. 11, No. 1, pp. 64-72.

Caira, Mino R., "Crystalline Polymorphism of Organic Compounds," Topics in Current Chemistry, 1998, vol. 198.

Priority Document for Indian Patent Application No. 978/MUM/2005 filed on Aug. 19, 2005.

Davey, R. J., "Solvent effects in crystallization processes," Current Topics in Materials Science, 1982, vol. 8, pp. 429-479.

English Translation of Office Action for European Application No. 06 090 095 dated Jan. 16, 2007.

Fuhrmann, Ulrike et al., "Synthesis and Biological Activity of a Novel, Highly Potent Progesterone Receptor Antagonist," J. Med. Chem, 2000, vol. 43, pp. 5010-5016.

Hazra, Braja G. et al., "Mifepristone (RU-486), the recently developed antiprogesterone drug and its analogues," J. Indian Inst. Sci. May —Jun. 2001, vol. 81, pp. 287-298.

Kyowa Hakko Kogyo Co Ltd., "Agent for increasing hemocyte corpuscle," Patent Abstracts of Japan, Publication Date: Jun. 29, 1999; English Abstracts of JP-11-171774.

Maibauer R. et al., "First human data for ZK 230211 (ZK-PRA), a new progesterone receptor antagonists: a phase 1 clinical analysis of safety and pharmacokinetics in healthy postmenopausal women," Abstracts-Poster Session IV, 2006.

Tellekson, David K. et al., "Strategies for Attacking and Defending Pharmaceutical Patents: A Modern Take on 'The Art of War'," 2005, vol. 17, No. 12, pp. 5-14.

Thomson Innovation Patent Record View, English Translation of Description and Claims retrieved on Aug. 20, 2010; English Abstract of EP0411733.

Thomson Innovation Patent Record View, English Translation of Description and Claims retrieved on Aug. 20, 2010; English Abstract of EP0676203.

Thomson Innovation Patent Record View, English Translation of Description and Claims retrieved on Aug. 20, 2010; English Abstract of WO98/026783.

Thomas Innovation Patent Record View, English Translation of Description and Claims retrieved on Aug. 20, 2010; English Abstract of WO99/053924.

Van Geerstein, J. V. et al., "Structure of the n-Butyl Acetate Solvate of 11β[4-(Dimethylamino)phenyl]-17β, hydroxy-17βhydroxy-17α-(1-propynyl)estra-4,9-dien-3-one," Acta. Cryst., C42, 1986, pp. 1521-1523.

Vippagunta, Sudha R. et al., "Crystalline Solids," Advanced Drug Delivery Reviews, 2001, vol. 48, pp. 3-26.

* cited by examiner

Fig. 1: DSC curve of the amorphous foam of 11β-(4-acetylphenyl)-20,20,21,21,21-pentafluoro-17-hydroxy-19-nor-17α-pregna-4,9-dien-3-one with an exotherm between 173°C and 185°C at a heating rate of 5 K/min.
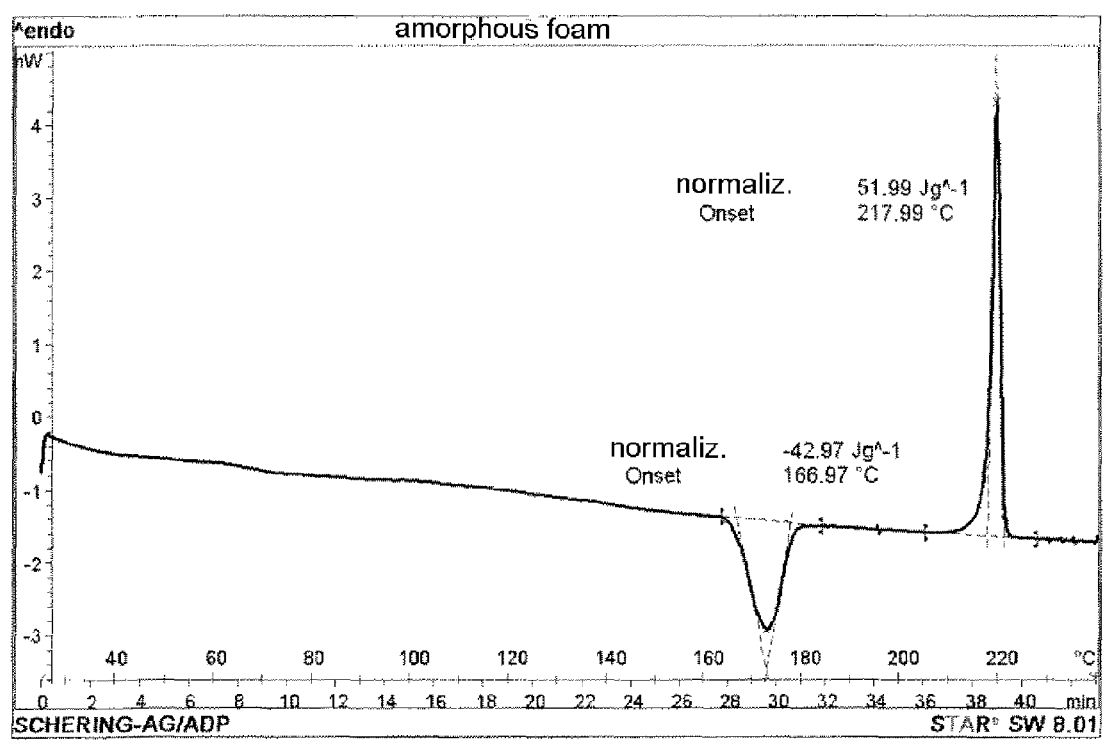

Fig. 2: X-ray powder diffractogram of the amorphous foam of 11β-(4-acetylphenyl)-20,20,21,21,21-pentafluoro-17-hydroxy-19-nor-17α-pregna-4,9-dien-3-one (CuK$_{\alpha 1}$ radiation)
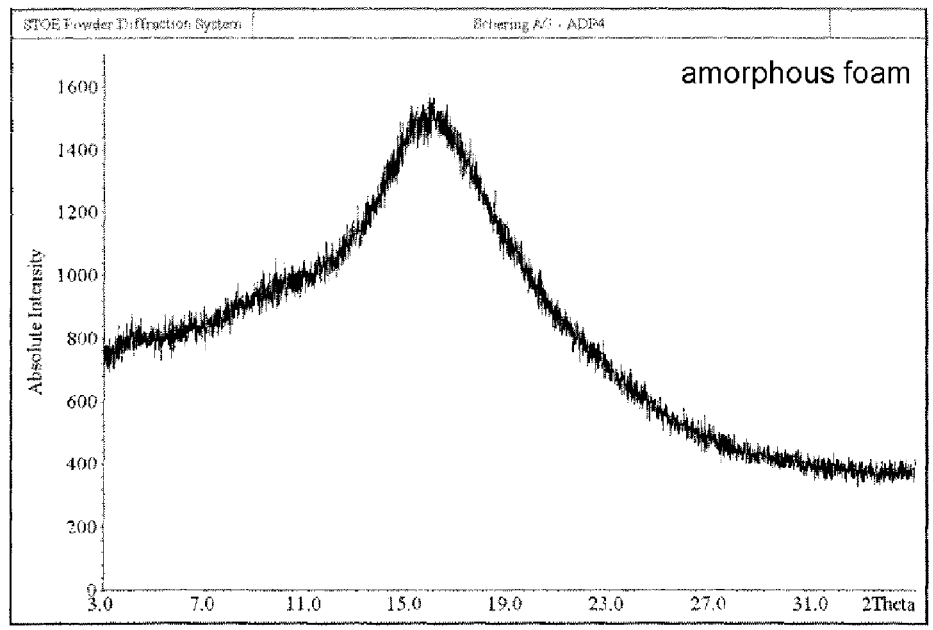
Fig. 3: X-ray powder diffractogram of polymorph I (CuK$_{\alpha 1}$ radiation)
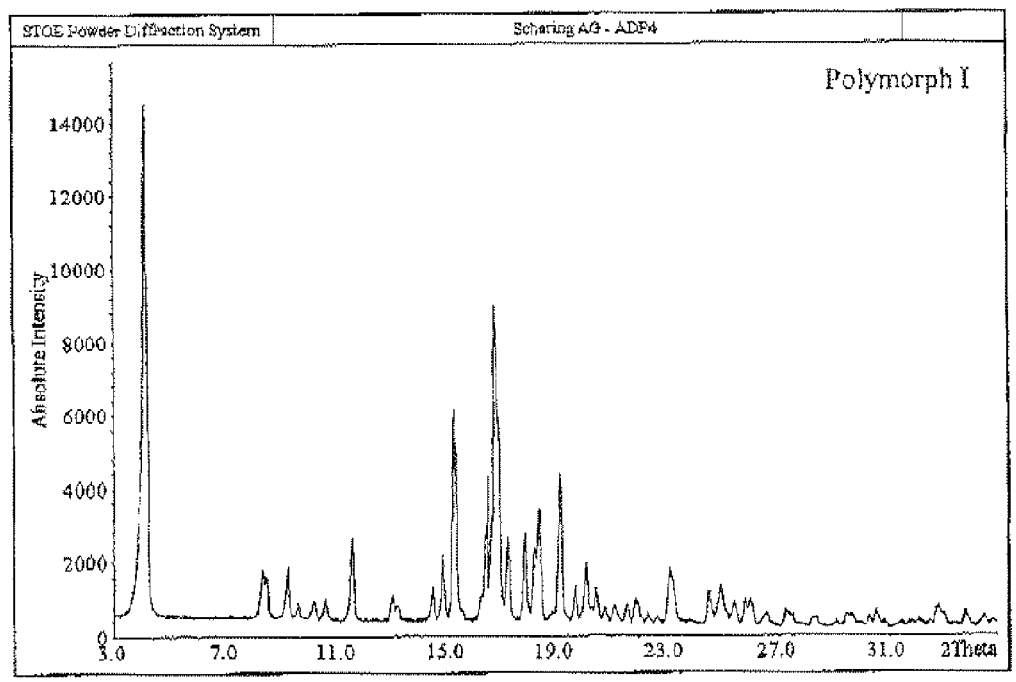

Fig. 4: DSC curve of polymorph I
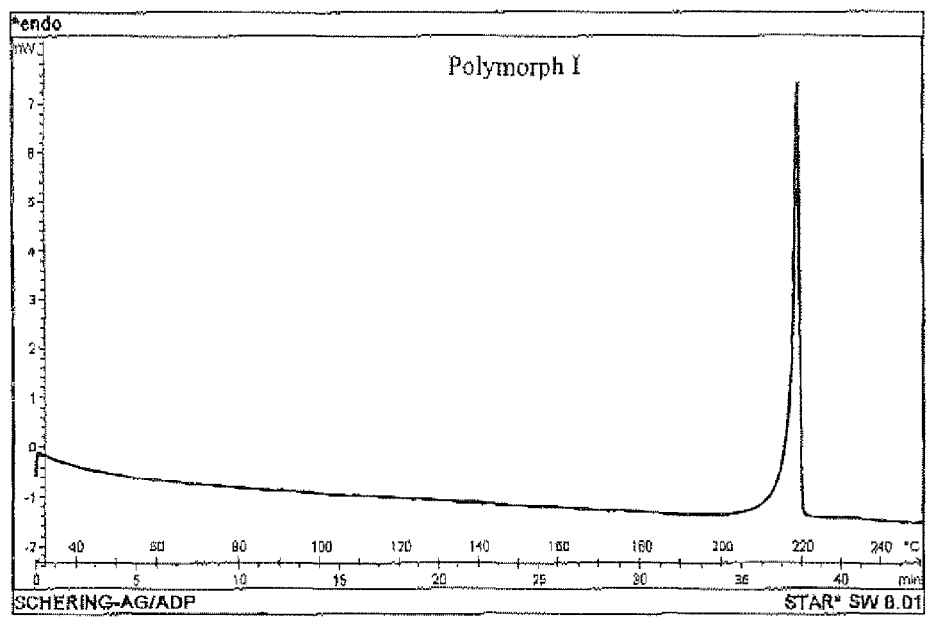

Fig. 5: IR spectrum of polymorph I (single-bounce ATR-IR)
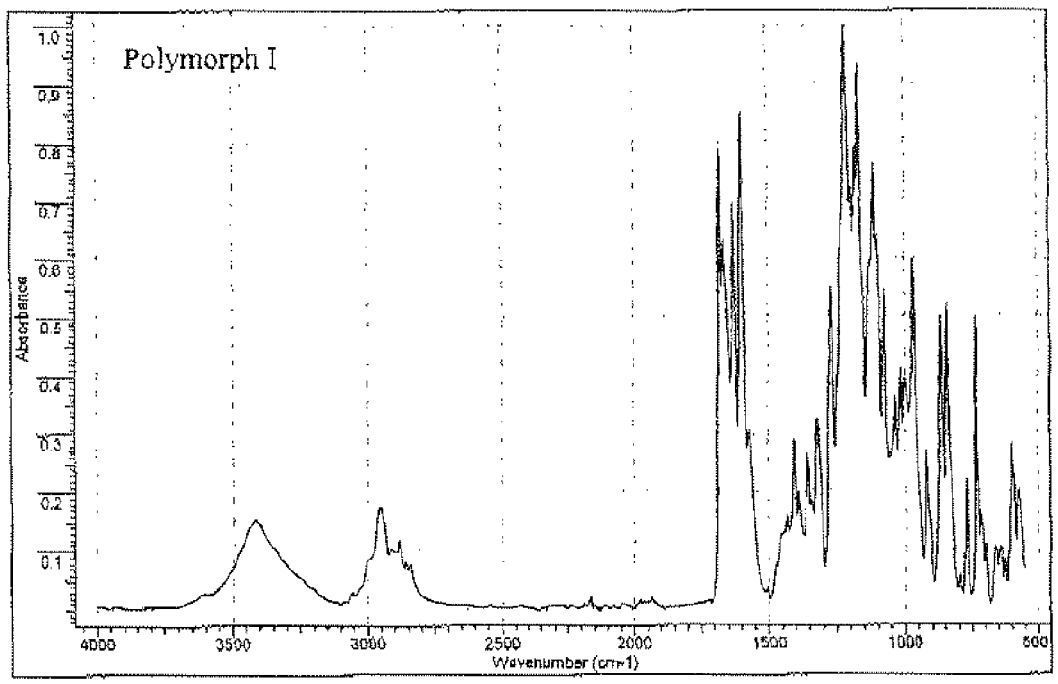
Fig. 6: Typical particle size distribution of polymorph I after grinding in an air jet mill
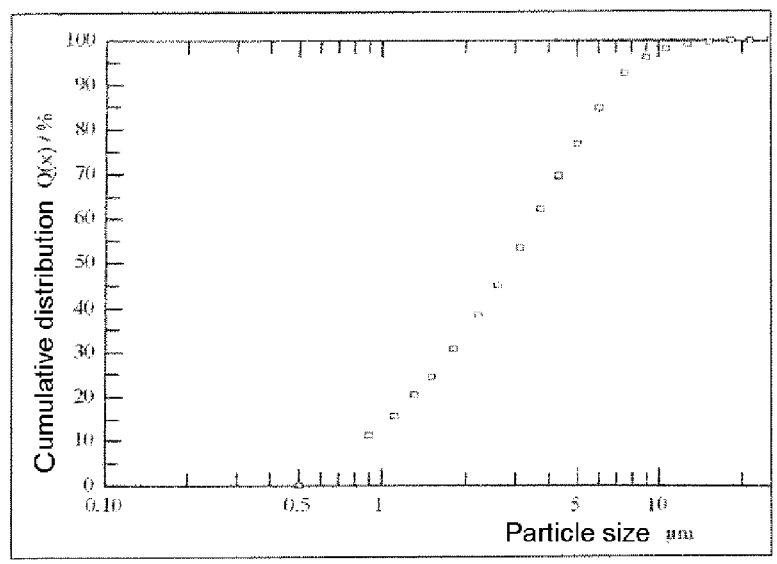

Fig. 7: Solubility of crystalline 11β-(4-acetylphenyl)-20,20,21,21,21-pentafluoro-17-hydroxy-19-nor-17α-pregna-4,9-dien-3-one as a function of the proportion of water in the water/ethanol mixture used as solvent
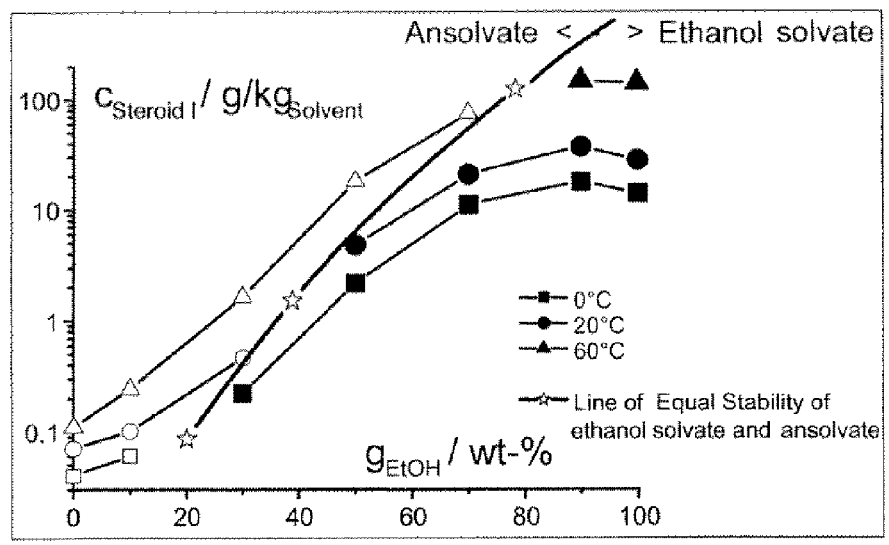
Fig. 8: X-ray powder diffractogram of the methanol solvate of 11β-(4-acetylphenyl)-20,20,21,21,21-pentafluoro-17-hydroxy-19-nor-17α-pregna-4,9-dien-3-one (CuK$_{\alpha 1}$ radiation)
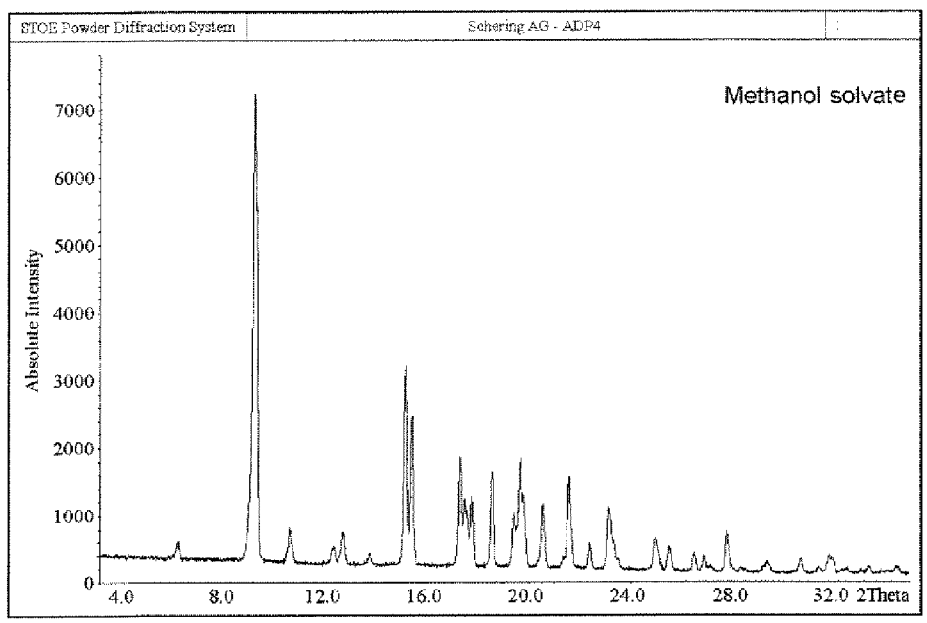

Fig. 9: X-ray powder diffractogram of the methanol solvate of 11β-(4-acetylphenyl)-20,20,21,21,21-pentafluoro-17-hydroxy-19-nor-17α-pregna-4,9-dien-3-one (CuK$_{α1}$ radiation)
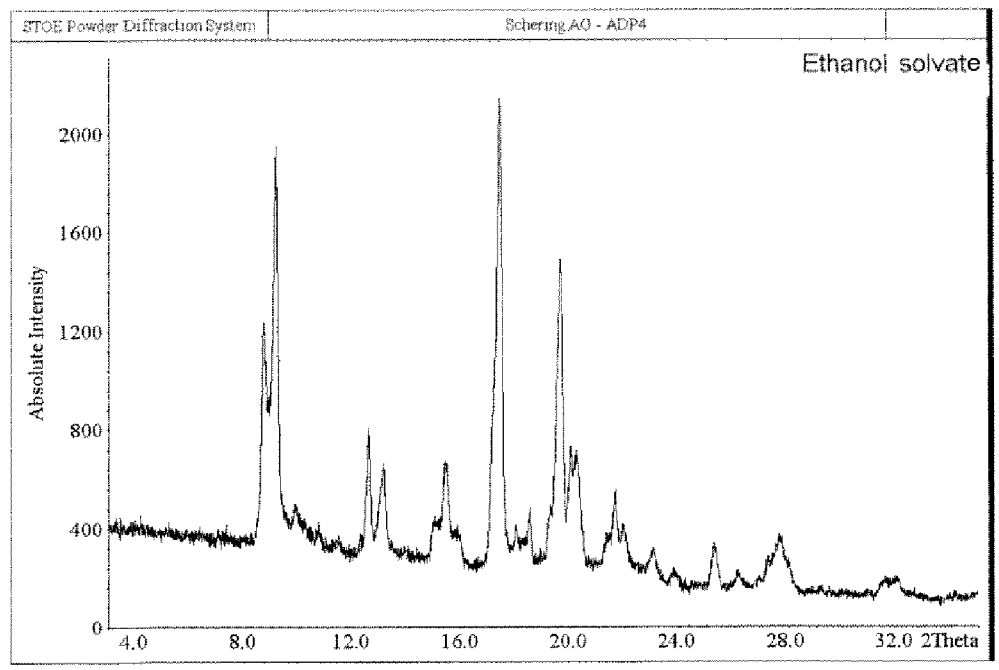
Fig. 10: X-ray powder diffractogram of polymorph II (CuK$_{α1}$ radiation)
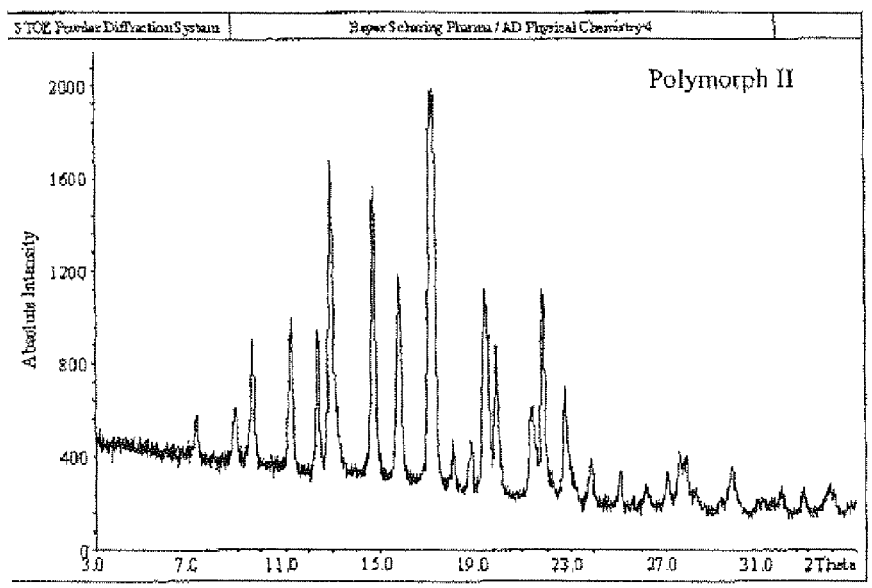

Fig. 11: DSC curve of polymorph II
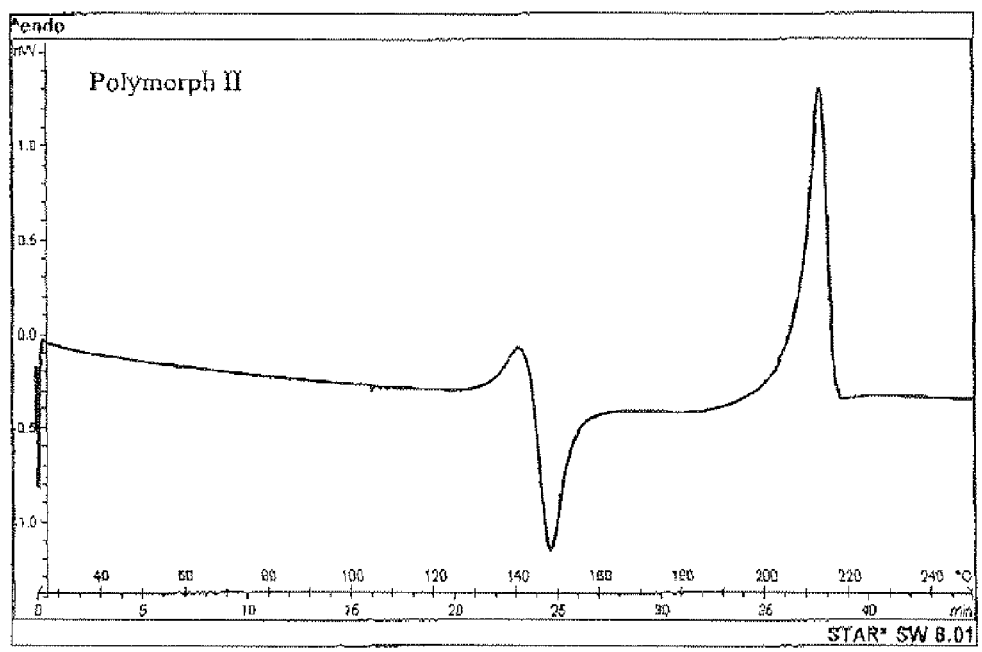
Fig. 12: IR spectrum of polymorph II (single-bounce ATR-IR)
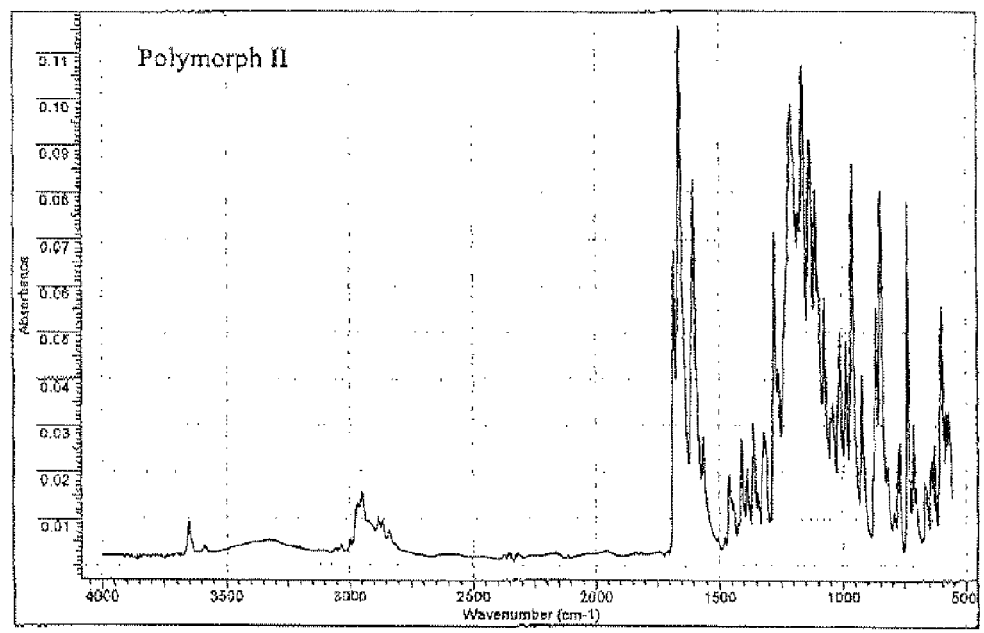

CRYSTALLINE FORMS OF 11β-(4-ACETYLPHENYL)-20,20,21,21,21-PENTAFLUORO-17-HYDROXY-19-NOR-17α-PREGNA-4,9-DIEN-3-ONE

This application claims the benefit of the filing date of U.S. Provisional Application Ser. No. 60/810,127 filed Jun. 2, 2006, which is incorporated by reference herein.

The present invention relates to crystalline forms of 11β-(4-acetylphenyl)-20,20,21,21,21-pentafluoro-17-hydroxy-19-nor-17α-pregna-4,9-dien-3-one. The invention relates in particular to two crystalline an solvate/anhydrate forms of this compound, polymorphs I and II. However, the present invention also relates to crystalline solvates, for example methanol and ethanol solvates of 11β-(4-acetylphenyl)-20,20,21,21,21-pentafluoro-17-hydroxy-19-nor-17α-pregna-4,9-dien-3-one as precursors for preparing these two polymorphs I and II. Processes for preparing polymorph I by displacement crystallization or by trituration are described. Selection of the last solvent before formation of the ansolvate can be based on the differences in the purification behaviour of the individual solvates of 11β-(4-acetylphenyl)-20,20,21,21,21-pentafluoro-17-hydroxy-19-nor-17α-pregna-4,9-dien-3-one. Polymorph I according to the invention is particularly suitable for the manufacture of medicinal products.

For active pharmaceutical ingredients to be processed into oral medicinal forms, these active ingredients must normally be in solid form. In this connection, a number of solid forms are possible. They may be amorphous or crystalline. On crystallization the active ingredient may result as ansolvate. It is likewise possible for a solvate to be formed through incorporation of solvents into the crystal. A hydrate is, for example, a solvate which has formed with incorporation of water into the crystal.

It is known that a number of physicochemical properties are determined by the respective solid form. Such properties of pharmaceutical relevance are for example the chemical stability of the active ingredient, its stability towards pharmaceutical excipients, its grindability and its flow behaviour. It is likewise known that crystalline solids have a greater stability than amorphous solids. With amorphous solids there is the risk of recrystallization and thus the risk of an uncontrolled loss of the solid form employed in the pharmaceutical formulation. The advantage of amorphous solids derives inter alia from their greater solubility or their distinctly increased rate of dissolution. When selecting the solid form to be used in a specific pharmaceutical formulation of an active ingredient it is necessary to balance the advantages and disadvantages against one another, for example in the rate of dissolution, the stability and the processability. A stable solid form is a prerequisite for developing a medicinal product because changes in properties are always also associated with conversion from one solid form into another.

Ansolvates and hydrates are acceptable as crystalline solids for pharmaceutical applications. Solvates of nonaqueous solvents are unsuitable as active ingredient because of the high organic solvent content—apart from a few exceptions.

The preparation of solid active pharmaceutical ingredients includes inter alia chemical synthesis, purification and isolation of the solid. Preparative chromatography is increasingly being employed for the purification. It is capable of depleting impurities to a large extent with negligible loss of active ingredient. This is particularly advantageous for impurities which are closely chemically related to the active ingredient and which can be depleted in classical crystallization only poorly or with large losses of active ingredient in the mother liquor. The active ingredient is in relatively dilute form in the raffinate of the preparative chromatography column. The active ingredient must be isolated from this raffinate in solid form.

11β-(4-Acetylphenyl)-20,20,21,21,21-pentafluoro-17-hydroxy-19-nor-17α-pregna-4,9-dien-3-one has the structural formula:

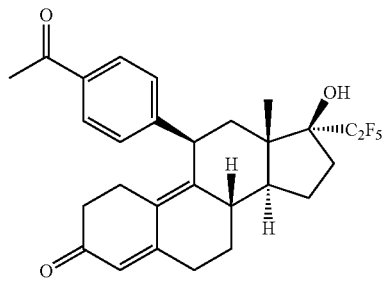

11β-(4-Acetylphenyl)-20,20,21,21,21-pentafluoro-17-hydroxy-19-nor-17α-pregna-4,9-dien-3-one has previously been disclosed only as amorphous foam (EP 0970103 B1, page 9, paragraph 0056). This amorphous foam results from concentration to dryness of the fractions containing the active ingredient after chromatography. The amorphous foams obtained in this way do not satisfy the requirements for an active pharmaceutical ingredient in relation to the content of residual solvents. In addition, removal of the foam from the stirrer is difficult. A further step on the route to the finished formulation is micronization. Micronization in this context is a fine grinding of the ground material, for example using an air jet mill. However, alternative processes for preparing microparticles are also suitable. This is necessary in particular with low-dose pharmaceutical preparations in order to ensure a uniform content of active ingredient in the formulation. A prerequisite for good grindability of a substance is inter alia an adequate flowability both of the starting material and of the ground material. Handling of the previously disclosed form is difficult here too, because it acquires an electrostatic charge and therefore can be micronized only with difficulty.

The usual way of generating a solid which can be handled, by crystallization from solutions, has not been possible to date. 11β-(4-Acetylphenyl)-20,20,21,21,21-pentafluoro-17-hydroxy-19-nor-17α-pregna-4,9-dien-3-one forms solvates on crystallization from solvents which are acceptable and conventional for crystallizing final stages and in which it is sufficiently soluble. The solvates have been detected after crystallization from organic solvents such as, for example, methanol, ethanol, isopropanol, acetone, 2-butanone, diisopropyl ether, dioxane or tetrahydrofuran, and from the solvent mixtures isopropanol/water, ethanol/ethyl acetate, isopropanol/isopropyl acetate. However, because of their content of residual solvent, these solvates do not satisfy the requirements for an active pharmaceutical ingredient. Drying to remove the solvent from the solvates formed in this way in turn leads to an amorphous phase.

It is generally known that the appearance of new, previously unknown solid forms of a known chemical compound is not predictable. The existence of crystalline phases is predictable just as poorly as the number of polymorphic forms. The possibility of forecasting the conditions for formation and properties of the individual forms is just as small.

It is an object of the present invention to generate solid forms of 11β-(4-acetylphenyl)-20,20,21,21,21-pentafluoro-17-hydroxy-19-nor-17α-pregna-4,9-dien-3-one which have neither the disadvantages of the known amorphous form, in particular the low storage stability and electrostatic charging during processing, nor the disadvantages of crystalline solvates with organic solvents.

The object has been achieved by finding polymorphs I and II.

It is known that amorphous solid forms do not show a well-defined and informative melting point. The DSC curve (DSC=differential scanning calorimetry) of the amorphous foam disclosed in EP 0970103 B1 showed, irrespective of the chosen heating rate, an exotherm between 110° C. and 200° C., followed by an endotherm at about 218° C. (compare FIG. 1). The solid present after the occurrence of the exotherm was investigated by XRPD (XRPD=X-Ray Powder Diffraction). It was thus possible to find a new, completely crystalline form which escapes identification in a classical screen but also in an HTS (HTS=high throughput screen) by forming solvates. FIG. 2 shows the X-ray powder diffractogram of the amorphous foam which shows no defined XRPD lines. FIG. 3 depicts the X-ray powder diffractogram of polymorph I according to the invention (transmission, Cu $K_{\alpha 1}$ radiation, 20-25° C.). This polymorph I shows an XRPD line d=21.4 Å. Further XRPD lines are located at 5.3 Å, 7.7 Å and 5.8 Å. FIG. 4 depicts the DSC curve of polymorph I which melts at about 218° C. The infrared spectrum (single-bounce ATR-IR) of polymorph I shows bands at 3416 $cm^{-1}$, 1680 $cm^{-1}$, 1628 $cm^{-1}$ and 1215 $cm^{-1}$ (see FIG. 5).

It was possible to prepare the polymorph I found in this way also on a larger scale (kg range). The processes used therefor are displacement crystallization using water and trituration.

The polymorph I according to the invention exhibits, besides the abovementioned advantages, a number of further properties which have beneficial effects on pharmaceutical processing. It does not acquire an electrostatic charge and can therefore be micronized without difficulty in an air jet mill. FIG. 6 shows a typical distribution curve of the ground material. A cumulative particle size distribution in which more than 50% of all the particles have a diameter of less than/equal to 3 μm (for the lower distribution, measured by the volume-based particle size distribution) (so-called $x_{50,3}$ value) can be achieved for the amorphous material only with great difficulty and especially not on an industrial scale, because the electrostatic charging and the poor flowability associated therewith makes specific metering into the mill extremely difficult.

The content of residual solvent falls further during micronization of polymorph I according to the invention. The corresponding values can be found in Table 1. The residual solvent content of polymorph I after micronization is 0.34-0.35% which is below the value of 0.5% recommended for ethanol in the ICH Q3C guideline (CPMP/ICH/283/95, 4.3, page 8/18). According to the X-ray powder diffractogram, there is no ethanol solvate whatsoever present in polymorph I before and after micronization.

TABLE 1

Ethanol content in polymorph I according to the invention before and after grinding in an air jet mill (micronization)

| Batch | Ethanol content | |
|---|---|---|
| | before grinding | after grinding |
| I | 1.08% | 0.35% |
| II | 1.00% | 0.34% |
| III | 1.24% | 0.35% |

The polymorph I exhibits a superior stability over the amorphous form. This is shown on comparison of the results of the temperature tests, moisture tests and in particular in light exposure tests. The decrease in the active ingredient content during storage at elevated temperature and elevated moisture is shown in Table 2. Before storage, the material employed had a content of 98.4% or of 95.4%.

TABLE 2

Comparison of the short-term stability of amorphous 11β-(4-acetylphenyl)-20,20,21,21,21-pentafluoro-17-hydroxy-19-nor-17α-pregna-4,9-dien-3-one and of polymorph I according to the invention on storage at elevated temperature and elevated humidity. The decrease in the active ingredient content is indicated.

| Temperature | rel. humidity | amorphous | | polymorph I | |
|---|---|---|---|---|---|
| ϑ | φ | 15 days | 30 days | 15 days | 30 days |
| 50° C. | | −2.9% | −5.1% | 0% | −0.3% |
| 50° C. | 75% | −2.8% | −3.3% | 0% | −0.1% |
| 70° C. | | −10.2% | −17.3% | −1.5% | −3.5% |
| 70° C. | 75% | −13.5% | −17.4% | −0.1% | −0.2% |
| 90° C. | | −32.6% | n. d. | −3.6% | n. d. |
| 90° C. | 75% | −31.7% | n. d. | −0.2% | n. d. |

The greater stability of polymorph I is even clearer on storage under light. Table 3 shows the stabilities after storage under 20 kLux for 42 hours and for 66 hours. The initial values were 98.4% and 95.4% here too.

TABLE 3

Comparison of the stability of amorphous 11β-(4-acetylphenyl)-20,20,21,21,21-pentafluoro-17-hydroxy-19-nor-17α-pregna-4,9-dien-3-one and of polymorph I on storage under light. The decrease in the active ingredient content is indicated.

| Duration | amorphous | polymorph I |
|---|---|---|
| 42 h | −34% | −0.2% |
| 66 h | −42% | −0.4% |

On use of 11β-(4-acetylphenyl)-20,20,21,21,21-pentafluoro-17-hydroxy-19-nor-17α-pregna-4,9-dien-3-one as active ingredient in pharmaceutical preparations, the profile of impurities is of crucial importance. A compound which occurs on storage of this active ingredient is 11β-(4-acetylphenyl)-20,20,21,21,21-pentafluoro-17-hydroxy-9,10-epoxy-19-nor-10α,17α-pregna-1,4-dien-3-one. The toxicity of this compound is known. The content of this impurity must be below 0.2% until the shelf life of the pharmaceutical formulation expires. There was found to be considerable formation of this impurity on storage of the amorphous solid of 11β-(4-acetylphenyl)-20,20,21,21,21-pentafluoro-17-hydroxy-19-nor-17α-pregna-4,9-dien-3-one under stress conditions (elevated temperature and humidity) and under light. The amorphous solid is therefore unsuitable without stabilization for use in a medicinal product. With polymorph I, however, the increase in this critical impurity is virtually zero. Elaborate stabilization on use of polymorph I is therefore no longer necessary. The formation of the abovementioned epoxy impurity on storage of amorphous 11β-(4-acetylphenyl)-20,20,21,21,21-pentafluoro-17-hydroxy-19-nor-17α-pregna-4,9-dien-3-one at a temperature of 70° C. is 0.6% after only 15 days and as much as 1.1% after 30 days. On the other hand, on storage of polymorph I at the same temperature for 30 days, just 0.1% of the epoxy impurity is detectable. Table 4 shows the increase in the epoxy impurity on storage of amorphous 11β-(4-acetylphenyl)-20,20,21,21,21-pentafluoro-17-hydroxy-19-nor-17α-pregna-4,9-dien-3-one under stress conditions and under light. By comparison therewith, polymorph I according to the invention shows an increase of less than 0.2% in these impurities.

TABLE 4

Increase in the epoxy impurity on storage of amorphous 11β-(4-acetylphenyl)-20,20,21,21,21-pentafluoro-17-hydroxy-19-nor-17α-pregna-4,9-dien-3-one and of polymorph I on storage under light.

| Condition | | amorphous | polymorph I |
|---|---|---|---|
| 20 kLux | 42 h | 8.4% | 0.1% |
| 20 kLux | 66 h | 11.2% | 0.1% |

Partial recrystallization to give polymorph I was found for the amorphous active ingredient under stress conditions (15 d, 90° C./75% relative humidity). It can be assumed that such a recrystallization also occurs on storage of the amorphous phase over a lengthy period at relatively low temperatures. Such a conversion is, however, undesired in the finished medicinal form because it may lead to an altered, non-reproducible release of the active ingredient, but may also influence the hardness of the medicinal form.

The polymorph I according to the invention can be processed to pharmaceutical preparations which can be employed for the treatment of myomas or of a breast carcinoma. It can be used as active ingredient in female contraception, but also for the treatment of gynaecological disorders such as dysmenorrhoea or endometriosis, for hormone replacement therapy, for inducing menstruation and for induction of labour. Because of its potent antitumour activity, it can also be employed in combination with an antioestrogen (concurrently or sequentially) in products for the treatment of hormone-dependent tumours (EP0310542). Use in the treatment of tumours in the bowel region, in the region of the prostate, of the ovary, of the endometrium, and of meningiomas, is also conceivable.

11β-(4-Acetylphenyl)-20,20,21,21,21-pentafluoro-17-hydroxy-19-nor-17α-pregna-4,9-dien-3-one forms solvates with the solvents which are suitable for this substance. There are two possible ways for preparing polymorph I according to the invention: it can be prepared firstly by displacement using water and secondly by mean of trituration.

The polymorph I according to the invention can be obtained by a displacement crystallization from an organic solvent. It is necessary in this case for 11β-(4-acetylphenyl)-20,20,21,21,21-pentafluoro-17-hydroxy-19-nor-17α-pregna-4,9-dien-3-one not to form a solvate with the antisolvent employed for displacement. It is also possible to employ as primary solvent those with which 11β-(4-acetylphenyl)-20,20,21,21,21-pentafluoro-17-hydroxy-19-nor-17α-pregna-4,9-dien-3-one forms a solvate but it is then necessary for the proportion of primary solvent to be reduced during the displacement so that the solvate becomes unstable. One possible antisolvent is water because 11β-(4-acetylphenyl)-20,20,21,21,21-pentafluoro-17-hydroxy-19-nor-17α-pregna-4,9-dien-3-one does not form hydrates. The proportion of water necessary to avoid formation of the solvate depends both on the primary solvent and on the temperature at which the crystallization is carried out. Table 5 shows for the primary solvent ethanol the necessary proportions of water in the ethanol as a function of temperature which are necessary as a minimum for reliable crystallization of polymorph I from ethanol. At room temperature (20° C.), for example 40 wt % water are necessary. 40 wt % means in this connection 40% by weight of water, i.e. 0.4 g of water are present per gram of solvent mixture.

TABLE 5

Proportion of water necessary as a minimum for reliable displacement crystallization of polymorph I as a function of temperature

| Temperature | Proportion of water |
|---|---|
| 0° C. | 20 wt % |
| 20° C. | 40 wt % |
| 60° C. | 80 wt % |

BRIEF DESCRIPTION OF THE DRAWINGS

FIG. 1 represents a DSC heating curve of an amorphous foam.
FIG. 2 represents an X-ray powder diffractogram of the amorphous foam.
FIG. 3 represents an X-ray powder diffractogram of polymorph I.
FIG. 4 represents a DSC curve of polymorph I.
FIG. 5 represents an IR spectrum of polymorph I.
FIG. 6 represents typical particle size distribution of polymorph I after grinding in an air jet mill.
FIG. 7 represents soluability of a crystalline material of the invention.
FIG. 8 represents an X-ray powder diffractogram of a methanol solvate of a compound of the invention.
FIG. 9 represents an X-ray powder diffractogram of a methanol solvate of a compound of the invention.
FIG. 10 represents an X-ray powder diffractogram of polymorph II.
FIG. 11 represents a DSC curve of polymorph II.
FIG. 12 represents an IR spectrum of polymorph II.

The solubility of 11β-(4-acetylphenyl)-20,20,21,21,21-pentafluoro-17-hydroxy-19-nor-17α-pregna-4,9-dien-3-one in a water/ethanol mixture shows a strong dependence on the proportion of water. This dependency is depicted in FIG. 7. The solubility of 11β-(4-acetylphenyl)-20,20,21,21,21-pentafluoro-17-hydroxy-19-nor-17α-pregna-4,9-dien-3-one has fallen to one-hundredth of the solubility in pure ethanol when the proportion of water is only 20 wt %. Hence, the described displacement is economically worthwhile for 11β-(4-acetylphenyl)-20,20,21,21,21-pentafluoro-17-hydroxy-19-nor-17α-pregna-4,9-dien-3-one. The required proportion of water is distinctly higher for other systems, so that the displacement can be carried out only at high dilution and thus with an inadequate space yield.

The polymorph I according to the invention can also be obtained by trituration. It is known that phase transitions between different solid forms are possible on trituration in a solvent of low solvent power. The transition in this case always leads to the solid which is more stable under the specific conditions. Trituration of solvates may lead to removal of the solvent of the salvation. For this purpose it is necessary to leave the stability domain for the solvate. As described above, 40 wt % water in ethanol are sufficient for this at room temperature. The solubility of 11β-(4-acetylphenyl)-20,20,21,21,21-pentafluoro-17-hydroxy-19-nor-17α-pregna-4,9-dien-3-one is sufficiently low in such a mixture, compare FIG. 7, so that the process can be carried out without great loss of substance. It is not possible theoretically to predict whether the new phase resulting from such a trituration is amorphous or crystalline. The described trituration results according to the invention in polymorph I.

The residue solvent contents after trituration in water and conversion into an ansolvate form are shown for three solvents in Table 6. In all cases, pure polymorph I was present after the desolvation.

TABLE 6

Residue solvent contents after trituration in water

| Starting material | Residue solvent content | Form |
|---|---|---|
| MEK solvate | 0.07-0.11% MEK | Polymorph I |
| Methanol solvate | <0.01% methanol | Polymorph I |
| Acetone solvate | 0.01% acetone | Polymorph I |
| MTBE solvate | 0.02% MTBE | Polymorph I |

Thus, a number of solvates are suitable as starting point for forming the ansolvate form. A selection can be based on further target variables. As has been found, depletion of impurities on formation of the different solvates varies in extent. It is therefore possible to improve the purification by the choice. The efficiency of depletion of impurities in the resolvation/recrystallization can be compared using both the total of impurities and specific impurities. Table 7 compares two effective solvents (methyl ethyl ketone [MEK], acetone) with the insufficiently depleting MTBE. A change in the total of impurities and the decrease in the largest and second largest impurity is indicated. The depletion factor covers the range from 7:1 to 2:1. The effectively depleting solvents also differ in the depletion of particular impurities, in this case the largest impurity. The yields are 85-90% for all triturations.

TABLE 7

Decrease in the total of impurities, in the content of the largest and in the content of the second largest impurity in the resolvation to give an MEK, acetone and MTBE solvate. The contents of impurity in the starting material (SM) and in the three products are indicated

| Solvent for trituration | Total impurities | | Largest impurity | | Second largest impurity | |
|---|---|---|---|---|---|---|
| | SM | Product | SM | Product | SM | Product |
| MEK | 9% | 2.2% | 1.7% | 0.24% | 0.8% | 0.15% |
| Acetone | 9% | 2.0% | 1.7% | 0.67% | 0.8% | 0.15% |
| MTBE | 9% | 5.9% | 1.7% | 1.2% | 0.8% | 0.55% |

Purification by resolvation/recrystallization can be carried out in accordance with Example 8.

Besides polymorph I mentioned above, it has been possible to prepare a further polymorph II (cf. Example 7). For this purpose, 11β-(4-acetylphenyl)-20,20,21,21,21-pentafluoro-17-hydroxy-19-nor-17α-pregna-4,9-dien-3-one was dissolved in hot ethanol. The ethanol solvate crystallized out on cooling the ethanolic solution. Thermal desolvation of the ethanol solvate results in polymorph II. It can be assumed that polymorph II is more stable than the amorphous form. However, since it is less thermodynamically stable than polymorph I, it is only the second choice of active ingredient in solid medicinal products.

FIG. 10 shows the X-ray powder diffractogram of polymorph II (CuK$_{\alpha1}$ radiation, 20-25° C.). Polymorph II shows a characteristic XRPD line d=5.1 Å. Further XRPD lines are located at 7.1 Å and 5.6 Å. FIG. 11 depicts the DSC curve of polymorph II, which melts at about 135° C. The melt of polymorph II recrystallizes as polymorph I, which melts at about 218° C. The infrared spectrum (single-bounce ATR-IR) of polymorph II shows bands at 3653 cm$^{-1}$, 1682 cm$^{-1}$, 1601 cm$^{-1}$ and 1209 cm$^{-1}$ (see FIG. 12).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLE 1

Recrystallization Under Thermal Stress

Between 2 mg and 10 mg of the amorphous material were heated in an open Al capsule under nitrogen in a DSC with heating rates between 1 K/min and 20 K/min. The thermogram shows a recrystallization exotherm which is followed by a fusion endotherm with an onset temperature of 218° C. (see FIG. 1).

EXAMPLE 2

Displacement Crystallization 115 kg of water are added over the course of 10 minutes to a solution of 12.5 kg of 11β-(4-acetylphenyl)-20,20,21,21,21-pentafluoro-17-hydroxy-19-nor-17α-pregna-4,9-dien-3-one in 120 l of ethanol at 60° C. and codistilled in vacuo at a jacket temperature of 60° C. The codistillation is repeated until the ethanol content in the vapour is below 1%. This is followed by cooling to 20° C. and subsequent stirring for 30 min. Removal of the solid and drying result in 11.9 kg of polymorph 1.

EXAMPLE 3

Displacement Crystallization with Purification 58 kg of water are added over the course of 5 minutes to a solution of 7.6 kg of 11β-(4-acetylphenyl)-20,20,21,21,21-pentafluoro-17-hydroxy-19-nor-17α-pregna-4,9-dien-3-one in 33 l of ethanol at the boiling point. This is followed by cooling to 2° C. and subsequent stirring for one hour. Removal of the solid and drying result in 6.2 kg of polymorph I.

With a yield of 93% in the displacement there was a depletion of certain impurities by a factor of about 3. Thus, 11β-(4-acetylphenyl)-17β-hydroxy-17α-methylestra-4,9-dien-3-one decreases from 1.1% to 0.38% and thus below specification. 63% of this impurity is subsequently present in the mother liquor.

EXAMPLE 4

Trituration 15.6 kg of the ethanol solvate (X-ray powder diffractogram: compare FIG. 9, preparation in analogy to Example 5) are triturated in 217 kg of water at an internal temperature of 85° C. for one hour. Followed by cooling to 25° C. Isolation and drying result in 12.7 g of polymorph I.

EXAMPLE 5

Trituration 585 mg of 11β-(4-acetylphenyl)-20,20,21,21,21-pentafluoro-17-hydroxy-19-nor-17α-pregna-4,9-dien-3-one are dissolved in methanol at 64° C. and obtained as methanol solvate by cooling to room temperature. Isolation and drying result in 463 mg of methanol solvate. FIG. 8 shows the X-ray powder diffractogram of the methanol solvate.

102 mg of this methanol solvate are triturated in 5 mL of water at 70° C. for 245 min. After 31 min, a sample is taken and dried at room temperature. The recorded X-ray powder diffractogram corresponds to the X-ray powder diffractogram of polymorph I (compare FIG. 3). The product contains less than 0.02% methanol.

EXAMPLE 6

Micronization 10 kg of polymorph I according to the invention, with a residual solvent content of slightly above 1% ethanol (compare Table 1), are ground with an air jet mill at a mass flow of 4 kg/h and with a grinding pressure of 5 bar at about 220 Nm$^3$/h. Specific metering of the ground material takes place without difficulty in the absence of electrostatic charging. The resulting product has a cumulative particle size distribution ($x_{50,3}$ value) of 3 μm. The residual solvent content has fallen to 0.35%.

EXAMPLE 7

Preparation of Polymorph II 1.2 g of 11β-(4-acetylphenyl)-20,20,21,21,21-pentafluoro-17-hydroxy-19-nor-17α-pregna-4,9-dien-3-one are dissolved in 6.12 g of ethanol at 70° C. and crystallized by cooling to −10° C. over the course of 2 hours. After subsequent stirring at −10° C. overnight, the crystals are isolated at −10° C. After drying in a convection drying oven with nitrogen blanketing at 40° C., 1.09 g of polymorph II are obtained after 16 hours.

EXAMPLE 8

Purification by Resolvation/Recrystallization 1000 mg of ethanol solvate are suspended in 5 ml of methyl ethyl ketone (MEK). The suspension is stirred at 90° C. for 30 minutes, then cooled to −15° C. over the course of 60 minutes, and stirred at this temperature for 60 minutes. The suspension is put onto a filter at −15° C. and filtered with suction. The yield is increased by rinsing the reaction vessel with 1 ml of methyl ethyl ketone at −15° C. and likewise putting the rinsed suspension on the filter.

The solid is dried in a convection drying oven at 40° C. 0.244 g of the MEK solvate prepared in this way is suspended in 2.05 ml of water at 70° C. for 2 hours. After cooling, 0.177 g of polymorph I is obtained after isolation and drying.

The entire disclosures of all applications, patents and publications, cited herein and of corresponding European application No. 06090095.8, filed Jun. 2, 2006, and U.S. Provisional Application Ser. No. 60/810,127, filed Jun. 2, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. Polymorph I of 11β-(4-acetylphenyl)-20,20,21,21,21-pentafluoro-17-hydroxy-19-nor-17α-pregna-4,9-dien-3-one, having an X-ray powder diffractogram showing lines at d=21.4 Å, d=7.7 Å d=5.8 Å and d=5.3 Å, and an IR spectrum showing bands at 3416 cm$^{-1}$, 1680 cm$^{-1}$, 1628 cm$^{-1}$ and 1215 cm$^{-1}$.

2. Polymorph II of 11β-(4-acetylphenyl)-20,20,21,21,21-pentafluoro-17-hydroxy-19-nor-17α-pregna-4,9-dien-3-one, having an X-ray powder diffractogram showing lines at d=5.1 Å, d=7.1 Å, and d=5.6 Å, and an IR spectrum showing bands at 3653 cm$^{-1}$, 1682 cm$^{-1}$, 1601 cm$^{-1}$ and 1209 cm$^{-1}$.

3. Pharmaceutical composition comprising polymorph I of crystalline 11β-(4-acetylphenyl)-20,20,21,21,21-pentafluoro-17-hydroxy-19-nor-17α-pregna-4,9-dien-3-one according to claim 1.

4. Pharmaceutical composition comprising polymorph II of 11β-(4-acetylphenyl)-20,20,21,21,21-pentafluoro-17-hydroxy-19-nor-17 α-pregna-4,9-dien-3-one, according to claim 2.

5. Pharmaceutical composition according to claim 3 comprising less than 0.2% 11β-(4-acetylphenyl)-20,20,21,21,21-pentafluoro-17-hydroxy-9,10-epoxy-19-nor-10α,17α-pregna-1,4-dien-3-one.

6. Process for preparing polymorph I according to claim 1 comprising displacement crystallizing said polymorph from an organic solvent that is ethanol with an antisolvent that is water with which 11β-(4-acetylphenyl)-20,20,21,21,21-pentafluoro-17-hydroxy-19-nor-17α-pregna-4,9-dien-3-one forms no solvate.

7. Process according to claim 6, where the proportion of water is above 50 wt % and the temperature is below 50° C.

8. Process for preparing polymorph I according to claim 1 comprising trituration of an organic solvate that is ethanol solvate in a solvent that is water, in which 11β-(4-acetylphenyl)-20,20,21,21,21-pentafluoro-17-hydroxy-19-nor-17α-pregna-4,9-dien-3-one forms no solvate.

9. Process according to claim 8, where the trituration is carried out at a temperature of 50-100° C.

10. Process according to claim 9, where the trituration is carried out at a temperature of about 80-90° C.

11. Process according to claim 8, wherein in the solvate impurities are depleted on preparation thereof.

\* \* \* \* \*